United States Patent

Lerner

[11] Patent Number: 5,938,643
[45] Date of Patent: Aug. 17, 1999

[54] DROP MONITORING UNIT FOR INFUSION SETS

[75] Inventor: Moshe Lerner, Petah Tikva, Israel

[73] Assignee: Unisor Multisystems Ltd, Petah Tikva, Israel

[21] Appl. No.: 08/891,075

[22] Filed: Jul. 10, 1997

[51] Int. Cl.⁶ .................................................. A61M 5/00
[52] U.S. Cl. ........................................ 604/253; 604/251
[58] Field of Search .................................. 604/253, 251, 604/30

[56] References Cited

U.S. PATENT DOCUMENTS

| | | |
|---|---|---|
| Re. 32,294 | 11/1986 | Knute . |
| 4,018,362 | 4/1977 | Ubaud . |
| 4,038,982 | 8/1977 | Burke et al. . |
| 4,314,484 | 2/1982 | Bowman . |
| 4,328,801 | 5/1982 | Marx et al. . |
| 4,469,480 | 9/1984 | Figler et al. . |
| 4,496,351 | 1/1985 | Hillel et al. . |
| 4,498,901 | 2/1985 | Finch . |
| 4,533,350 | 8/1985 | Danby et al. . |
| 4,775,368 | 10/1988 | Iwatschenko . |
| 5,152,424 | 10/1992 | Weinreb et al. . |
| 5,267,978 | 12/1993 | Dirr, Jr. . |

*Primary Examiner*—Wynn Wood Coggins
*Assistant Examiner*—N. Kent Gring
*Attorney, Agent, or Firm*—Benjamin J. Barish

[57] ABSTRACT

A drop monitoring unit for monitoring the rate of drop formation in an infusion set includes an attaching section at its upper end for attaching the drop monitoring unit to the inlet tube of the infusion set, and a pair of spaced parallel arms depending below the attaching section to straddle the opposite sides of the drip chamber, one of the arms including a light transmitter, and the other including a light receiver.

20 Claims, 8 Drawing Sheets

DROP MONITORING UNIT FOR INFUSION SETS

FIELD AND BACKGROUND OF THE INVENTION

The present invention relates to infusion systems, and particularly to a drop monitoring unit for monitoring drop formation and/or volume of infusion in an infusion set.

A wide number of drop monitoring units have been developed for infusion sets, as described for example in U.S. Pat. Nos. 4,018,362, 4,038,982, 4,314,484, 4,328,801, Re 32,294 of U.S. Pat. No. 4,397,648, 4,469,480, 4,496,351, 4,498,901, 4,533,350, 4,775,368, 5,152,424 and 5,267,978. The known devices, however, generally are incorporated into the construction of the drip chamber or require a specific construction of a drip chamber, and therefore are not capable of being applied as add-on units to existing infusion sets. Other known constructions are relatively complicated and therefore expensive to produce.

OBJECTS AND BRIEF SUMMARY OF THE INVENTION

An object of the present invention is to provide a drop monitoring unit having advantages in one or more of the above respects.

According to one aspect of the present invention, there is provided a self-contained drop monitoring unit attachable to, for monitoring drop formation in, an infusion set including a drip chamber to be supported in a vertical position, an inlet tube at the upper end of the drip chamber connectible to a supply of infusion liquid, and an outlet tube at the lower end of the drip chamber connectible to a patient to receive the infusion liquid. The drop monitoring unit includes an attaching section at its upper end for attaching the drop monitoring unit to the inlet tube of the infusion set; and a pair of spaced arms depending below the attaching section to straddle the opposite sides of the drip chamber. One of the arms includes a light transmitter, and the other includes a light receiver for optically sensing, and for producing an electrical output corresponding to, the interruptions in the light emitted from the light transmitter caused by the drops formed in and dropping through the drip chamber. The drop monitoring unit further includes an electrical circuit for energizing the light transmitter and for processing the electrical output of the light receiver to produce an output related to the sensed drop formation in the drip chamber; and a housing for an electrical battery for powering the electrical circuit, light transmitter and light receiver.

According to further features in the described preferred embodiments, the drop monitoring unit includes an electrical circuit housing on the front side of the unit for housing the electrical circuit, the battery housing being on the rear side of the unit. The pair of spaced parallel arms depend from one of the housings and are oblique to the longitudinal axis of the drip chamber such that the light transmitter and light receiver at the lower ends of the two arms are aligned with each other and with the vertical axis of the drip chamber.

As will be described more particularly below, a drop monitoring unit constructed in accordance with the foregoing features does not require any specific construction of the infusion set, or the drip chamber therein, and therefore may be provided a self-contained add-on unit to existing infusion sets. Moreover, the drop monitoring unit may be conveniently applied to an infusion system already set up for operation, and does not require its disassembly. Further, the provision of the front and rear housings, with the two depending arms straddling the opposite sides of the drip chamber, provides a compact, weight-balanced structure, which may be conveniently applied to, and stably supported by, the infusion sets.

According to further features in the described preferred embodiments, the attaching section includes a pair of spring elements engageable with the opposite sides of the inlet tube for clamping the drop monitoring unit thereto.

According to still further features included in preferred embodiments described below, the drop monitoring unit includes an indicator actuatable to indicate variations in the monitored rate of drop formation with respect to a reference rate. In some described embodiments, the drop monitoring unit further includes a user input device for presetting the reference rate; and in another described embodiment, it includes a processor enabling the reference rate to be preset by a "Learning" mode of operation.

According to another aspect of the present invention, there is provided a drop monitoring unit for monitoring the rate of drop formation in an infusion set, including a light transmitter for transmitting pulses of light through the drip chamber, a light receiver for optically sensing, and for producing an electrical output corresponding to, the interruptions in the light from the light transmitter caused by the drops formed in and dropping through the drip chamber, and an electrical circuit for energizing the light transmitter and for processing the electrical output of the light receiver to produce an output related to the sensed rate of drop formation in the drip chamber. The electrical circuit includes a light modulator which controls the light transmitter to transmit light pulses; a charging circuit enabled by the light modulator to receive the electrical output from the light receiver during the intervals between the transmitted light pulses, and to output short-duration pulses in the absence of a drop and longer-duration pulses in the presence of a drop; a drop detector circuit for storing a reference time Ta corresponding to that of a reference pulse indicating the absence of a drop, for measuring the sensed time T of the pulses outputted by the charging circuit, and for determining a drop to be present when the sensed time T is greater than the reference time Ta by a predetermined amount; and a drop rate calculator for calculating the drop rate from the output of the drop detector circuit.

As will be described more particularly below, the drop monitoring unit may take a large number of constructions, including a simple construction for use as a single-use disposable unit, a more complicated construction for use as a multiple-use disposable unit, and an even more complicated construction for use as a multiple use non-disposable unit capable of many additional functions.

Further features and advantages of the invention will be apparent from the description below.

BRIEF DESCRIPTION OF THE DRAWINGS

The invention is herein described, by way of example only, with reference to the accompanying drawings, wherein:

FIG. 7 is a timing diagram, and

DESCRIPTION OF PREFERRED EMBODIMENTS

Figure 1:
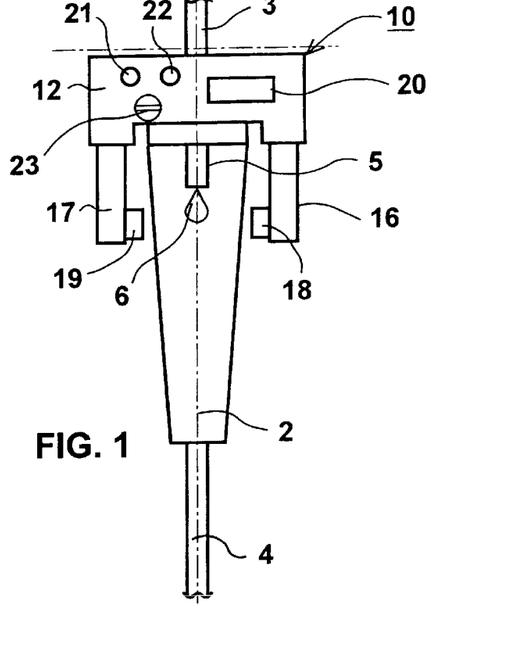
FIG. 1 is a front elevational view illustrating one form of drop monitoring unit constructed in accordance with the present invention.
Figure 2:
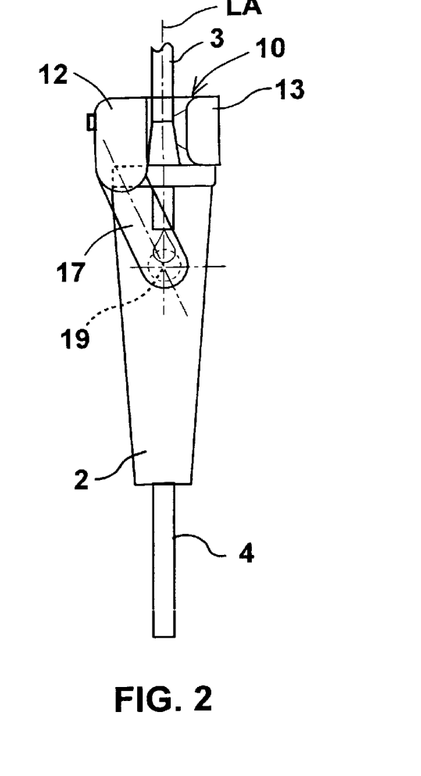
FIG. 2 is a side elevational view illustrating the drop monitoring unit of FIG. 1.
Figure 3:
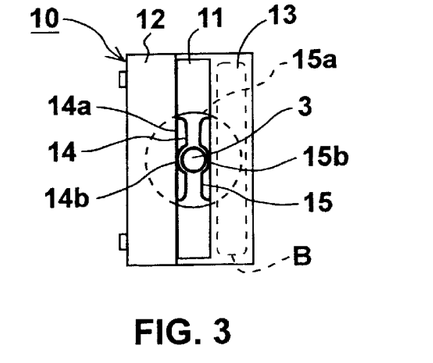
FIG. 3 is a top plan view illustrating the drop monitoring unit of FIG. 1.

The drop monitoring unit illustrated in FIGS. 1–3 is designed for use as an inexpensive, disposable self-contained add-on unit to be applied to a conventional infusion set which includes a transparent drip chamber 2 to be supported in a vertical position, an inlet tube 3 at its upper end connectible to a supply of infusion liquid (not shown), and an outlet tube 4 at its lower end connectible to a patient (not shown) to receive the infusion liquid. Drip chamber 2 is further formed with a hollow tubular inlet 5 at its upper end connectible to the inlet tube 3 for receiving the infusion liquid which forms drops 6 falling by gravity to the bottom of the drip chamber. The rate of feed of the infusion liquid to the patient is indicated by the rate of formation of the drops 6 viewable via the transparent walls of the drip chamber.

Since such an infusion set is well known, further details of its construction and operation are not set forth herein.

The present invention provides a self-contained drop monitoring unit, generally designated 10 in FIGS. 1–3, which may be conveniently applied to the infusion set in order to monitor the rate of drop formation in the drip chamber 2. For this purpose, the drop monitoring unit 10 includes a front housing 12 on the front side of the unit, and a rear housing 13 on the rear side of the unit. Front housing 12 is used for mounting the various electrical and optical components of the drop monitoring unit as will be described more particularly below, while the rear housing 13 is used for enclosing electrical batteries B energizing the various electrical and optical components.

The rear face of front housing 12 includes a spring element 14, and the front face of the rear housing 13 includes a similar spring element 15. The two spring elements 14, 15 are used for mounting the drop monitoring unit 10 to the inlet tube 3 of the infusion set.

Figure 4:
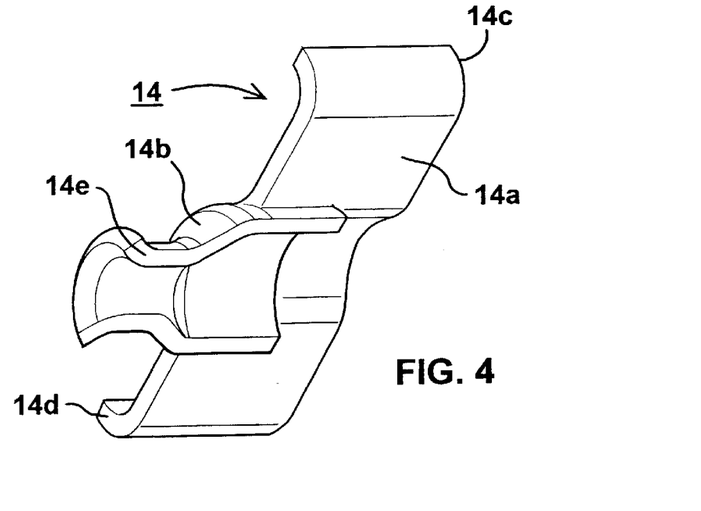
FIG. 4 is a three-dimensional view illustrating a construction of one of the spring elements used for attaching the unit of FIGS. 1–3 to the infusion set.

FIG. 4 more particularly illustrates a preferred construction for the spring element 14, it being appreciated that spring element 15 is similarly constructed. Thus, as shown in FIG. 4, spring element 14 includes a mounting section 14a for mounting it to the rear face of housing 12, and an attaching section 14b engageable with the inlet tube 3 when the drop monitoring unit 10 is attached to it. The two sections 14a, 14b are integrally formed of elastic material, preferably plastic or metal. The attaching section 14a is formed with outturned ends 14c, 14d for reception within grooves formed in the rear face of the front housing 12. The attaching section 14b is of shaped semi-cylindrical configuration formed with a smaller-diameter central portion 14e for engaging the inlet tube 3.

Figure 12:
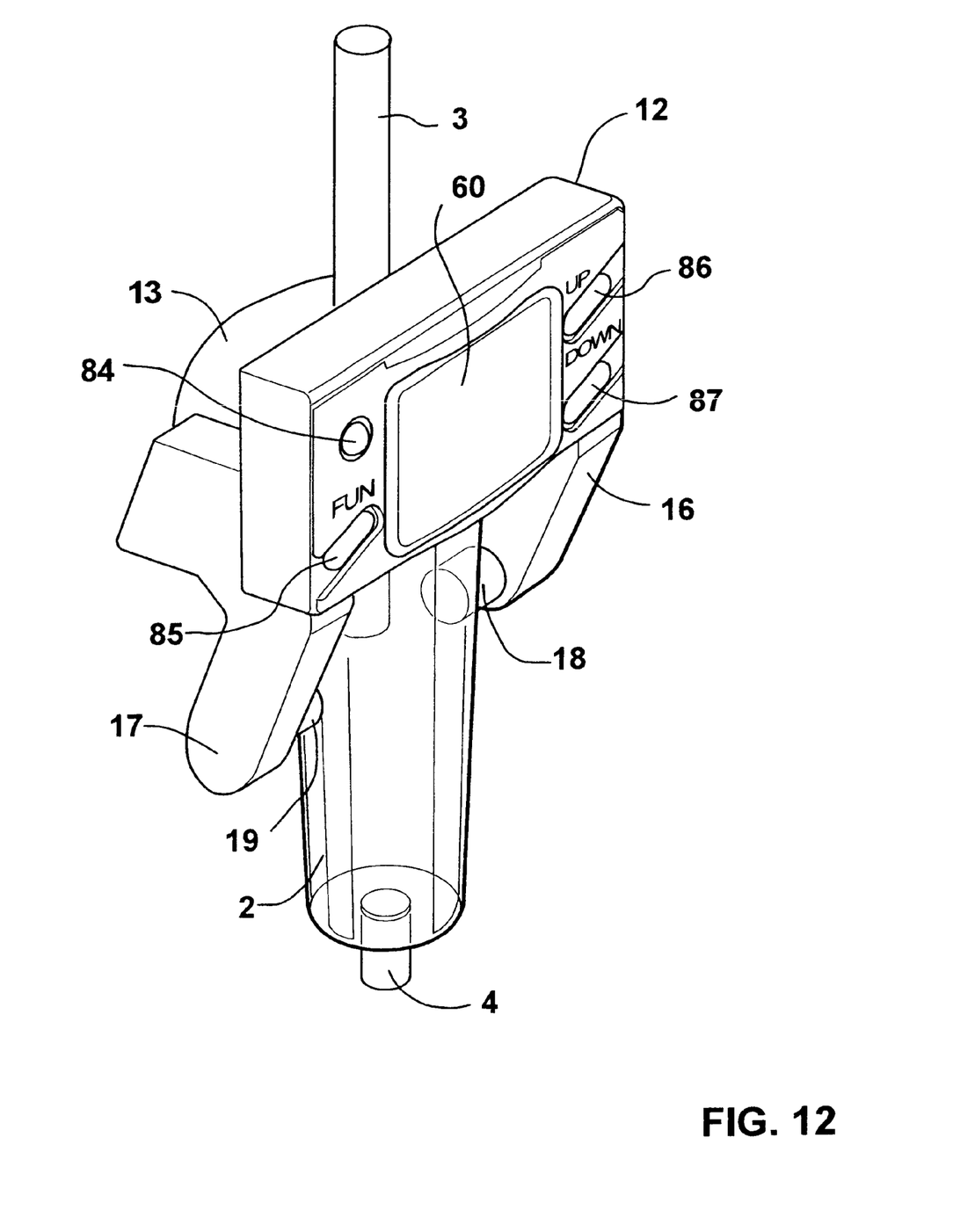
FIGS. 12 and 13 are pictorial illustrations, from the front and side, respectively, of another form of drop monitoring unit constructed in accordance with the present invention.
Figure 13:
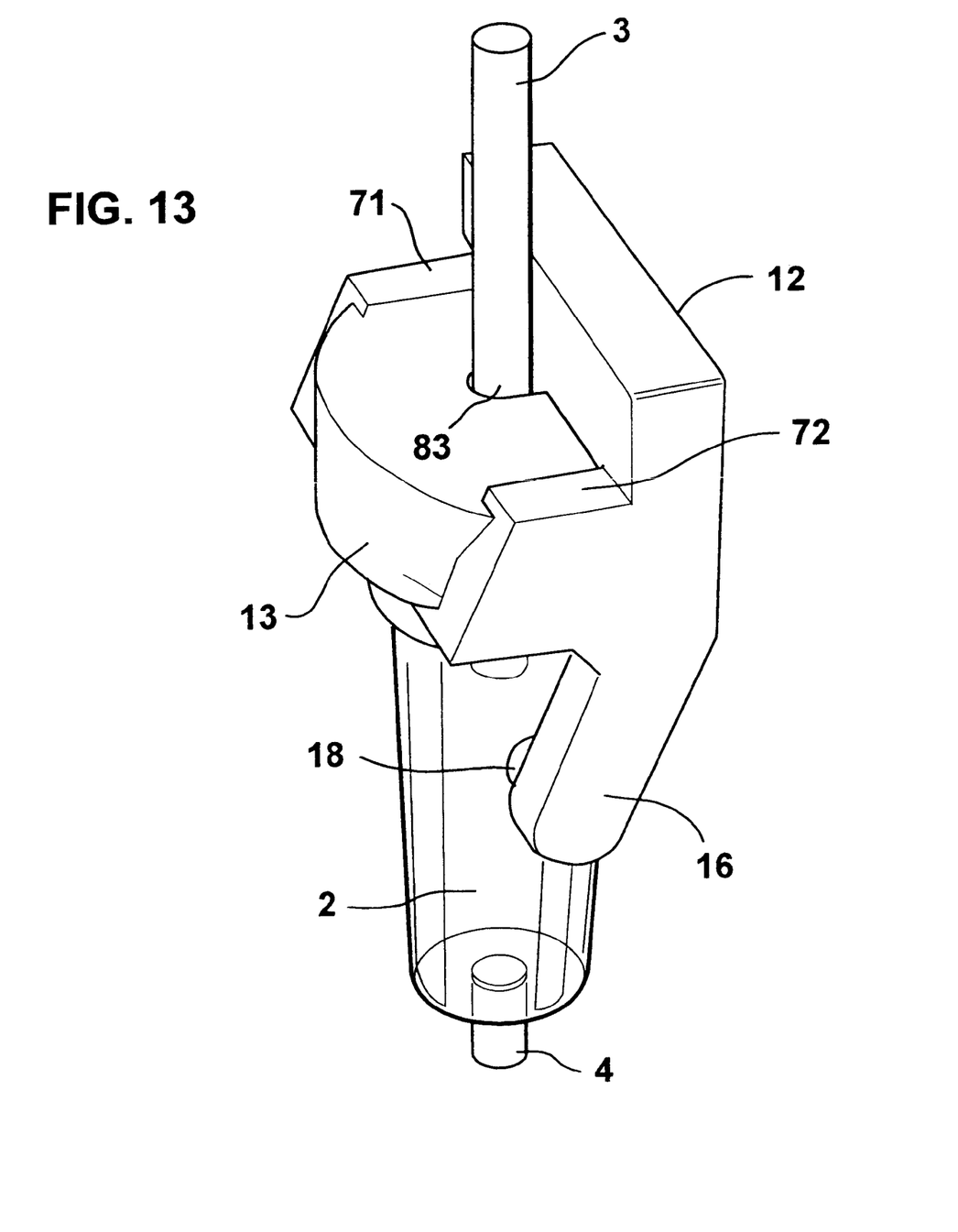

Spring element 15 is similarly constructed, to include a mounting section 15a attachable to the front face of the rear housing 13, and a shaped section 15b engageable with the inlet tube 3 when the drop monitoring unit 10 is attached to it. Preferably, the rear housing 13, containing the battery, is slidably attachable to the front housing 12, e.g., as illustrated in FIGS. 12 and 13, to be described below.

The drop monitoring unit 10 further includes a pair of spaced parallel arms 16, 17, depending from the front housing 12 so as to straddle the opposite sides of the drip chamber 2 when the drop monitoring unit 10 is mounted to the inlet tube 3. Arm 16 carries at its lower end a light transmitter 18, and arm 17 carries at its lower end a light receiver 19 to be in alignment with light transmitter 18. As shown particularly in FIG. 2, the two parallel arms 16, 17 depending from the front housing 12 extend obliquely to the longitudinal axis LA of the drip chamber such that the light transmitter 18 and the light receiver 19 are aligned with each other and with the longitudinal axis of the drip chamber.

The light transmitter 18 may be a source of IR (infrared) light, such as an LED or a laser; and the light receiver 19 may be a photodetector. Preferably, both operate in the near IR spectrum, e.g., 0.7–1 micron wavelength.

The front housing 12 mounts the electrical circuitry and the user interface devices. In the embodiment illustrated in FIGS. 1–3, the user interface devices include a Learn key 20, a green LED indicator 21, a red LED indicator 22, and a buzzer 23.

Figure 5:
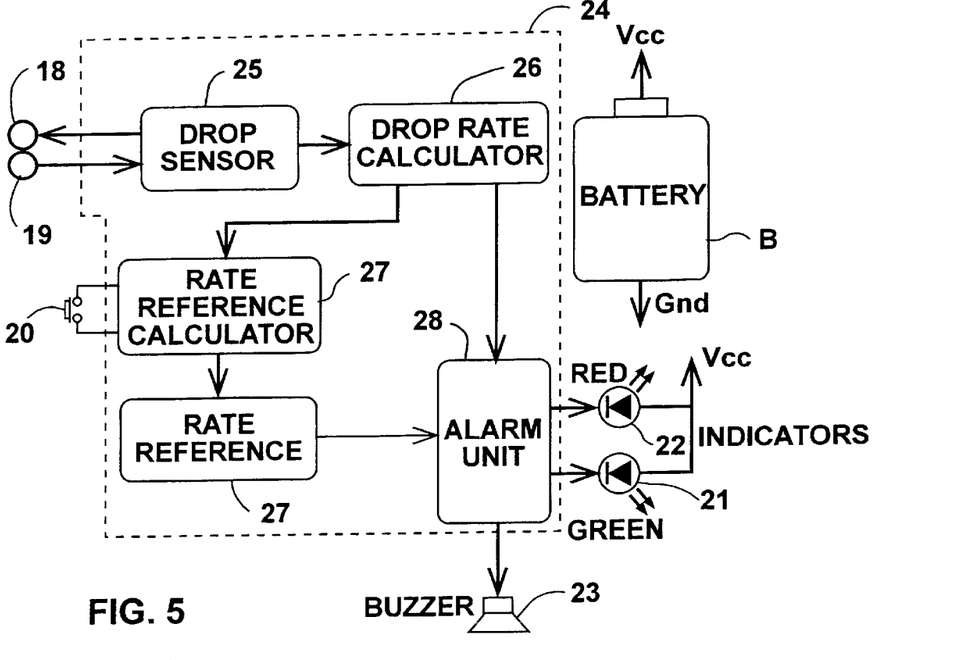
FIGS. 5 and 6 are block diagrams illustrating the electrical circuit in the unit of FIGS. 1–4.
Figure 6:
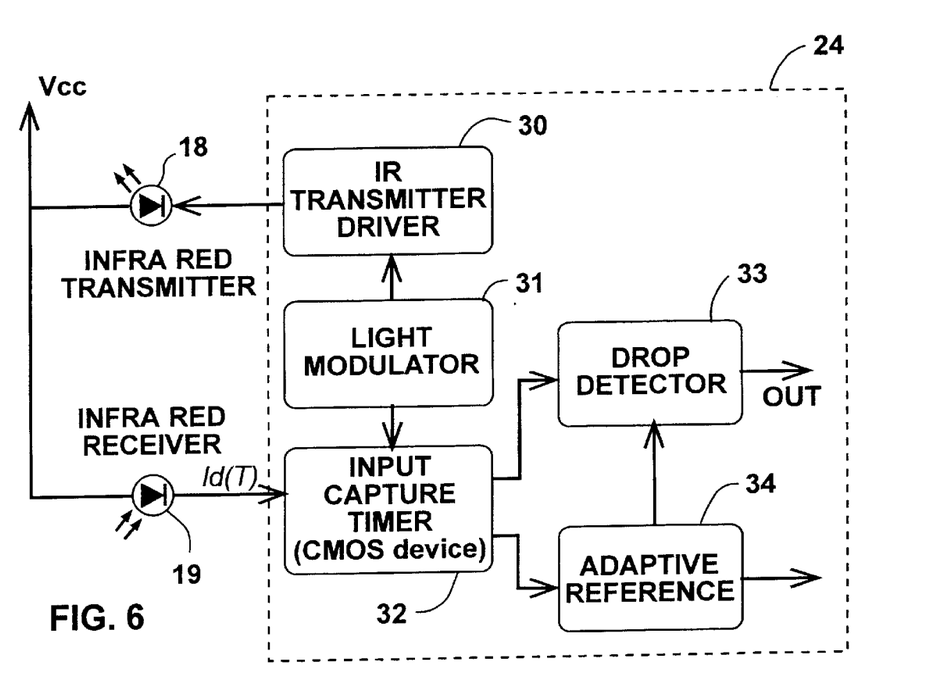

FIGS. 5 and 6 are block diagrams illustrating the electrical circuit in housing 12 of the drop monitoring unit of FIGS. 1–3. This electrical circuit includes a drop analyzer processor 24 performing the functions of (as shown schematically in FIG. 5) a drop detector 25, a drop rate calculator 26, a reference rate calculator 27 producing a reference rate signal 27a, and an alarm unit 28. Drop analyzer processor 24 is controlled by inputs from the IR receiver 19 and the Learn key 20, and in turn controls the IR transmitter 18, the green LED 21, the red LED 22, and the buzzer 23.

Drop analyzer processor 24 is programmed such that when the Learn key 20 is pressed, the unit operates according to the Learn mode for a predetermined period of time, e.g., one minute, during which it learns the average drop rate as sensed by the IR receiver 19 and automatically stores this value as a reference in rate reference calculator 25. After the predetermined time period, the unit returns automatically to a Normal mode, during which it senses the drops, automatically calculates the average current drop rate in drop rate calculator 26, compares it with the calculated reference rate stored in storage circuit 27, and if there is a discrepancy beyond a predetermined threshold, initiates the Alarm mode in alarm unit 28. During the Alarm mode, the buzzer 23 is energized to produce rapid short beeps, and the red LED 22 is caused to blink at the detected drop rate, i.e., fast at an excessively high drop rate, and slow at an excessively low drop rate.

The green LED 21 is controlled by drop analyzer processor 24 so that the LED is energized continuously during the Learn mode, and is caused to blink during the Normal mode at the detected drop rate.

FIG. 6 more particularly illustrates the construction of the drop analyzer processor 24. It includes an IR transmitter driver 30 controlled by a light modulator 31 to cause the IR transmitter 18 to transmit light pulses. Drop analyzer processor 24 further includes an input capture timer 32, preferably a CMOS device, containing a charging circuit enabled by light modulator 31 to receive the electrical output from the light receiver 19 during the transmission of light pulses by the IR transmitter 18. The input capture timer 32 controls a drop detector 33, and also an adaptive reference circuit 34. Drop detector 33 senses the output of the capture timer 32, and compares the output with an adaptive reference in circuit 34, to determine whether an output from the capture timer 32 indicates the presence or the absence of a drop. If a drop is determined to be present, drop detector 33 produces an output to the drop rate calculator 26 (FIG. 5).

Figure 7:
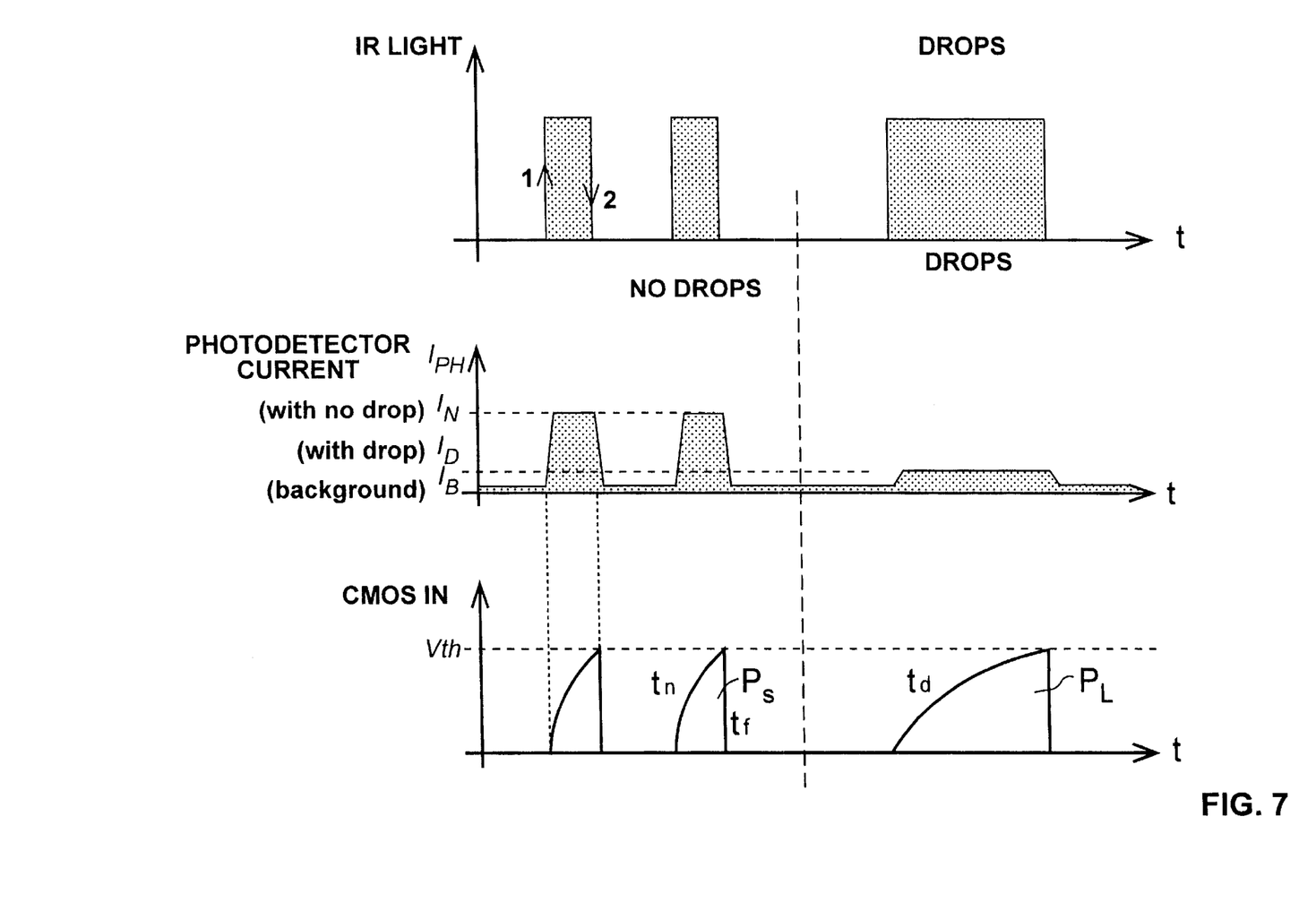
Figure 8:
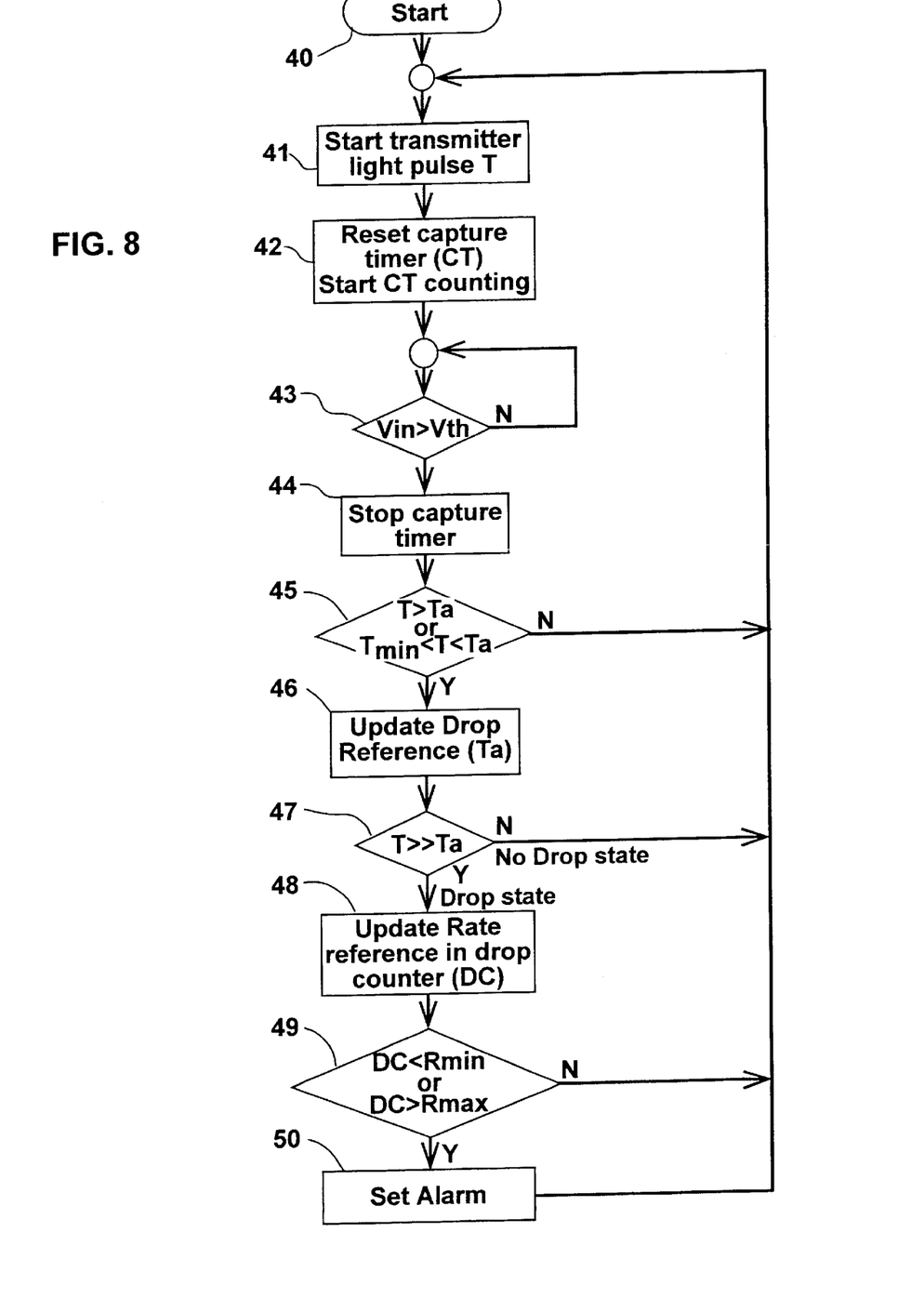
FIG. 8 is a flow chart, explaining the operation of the drop detector circuit in the unit of FIGS. 1–4.

The diagram of FIG. 7 and the flow chart of FIG. 8 more particularly illustrate the operation of drop analyzer processor 24. Thus, when no drop is detected, the light received by IR receiver 19 quickly charges the input capture timer 32 to its threshold, which then discharges to produce the short pulse $P_S$. However, when a drop is detected, the input capture timer 32 is more slowly charged to its threshold before it is discharged, to produce longer pulses $P_L$. In order to determine whether a pulse is a short pulse $P_S$ not to be counted as a drop, or a long pulse $P_L$ to be counted as a drop, the time T of each so-produced pulse is compared to a reference time Ts, which reference time is self-adaptive to the prevailing ambient conditions.

The flow chart of FIG. 8 more particularly illustrates the operation of the drop detector circuit 33, which determines whether a pulse outputted by the capture timer 32 is to be counted as a drop. In the flow chart of FIG. 8, the following legends apply:

T=Light pulse width
CT=Capture timer
Vin=CMOS device input voltage
Vth=CMOS threshold voltage
Tmin=Minimum pulse width
Ta=Average pulse width (No drop state)
DC=Drop counter
Rmin=Minimum Drop Rate
Rmax=Maximum Drop Rate At the start, the light modulator 31 initiates a light pulse from the IR transmitter 18 (block 41) and also resets the capture timer 32 (block 42). The light pulse is received by the IR receiver 19 which charges the CMOS device in the capture timer 32. When the charge reaches the threshold voltage of the CMOS device (block 43), the capture timer is interrupted (block 44), and the time (T), indicating the width of the light pulse outputted by the capture timer (per FIG. 7), is compared to the time Ta of the reference pulse (block 45). If T is greater than Ta, the time Ta of the reference pulse is incremented; and if T is less than Ta (but greater than $T_{min}$), the reference time Ta is decremented. Thus, the reference time Ta continuously changes with changing ambient conditions so as to be self-adaptive according to the prevailing conditions.

When the time T of the sensed pulse is compared with the reference time Ta, if T is much larger than Ta (i.e., larger than the incrementing and decrementing amounts), the sensed pulse is determined to represent a drop (block 47).

The sensed drop rate is compared with a reference drop rate in the rate reference circuit 27 (block 48). If the counted rate is less than the minimum reference rate or more than the maximum reference rate (block 49), the alarm is actuated (block 50). This alarm may be the buzzer 23 as well as the red indicator light 22 in FIG. 5.

Figure 9:
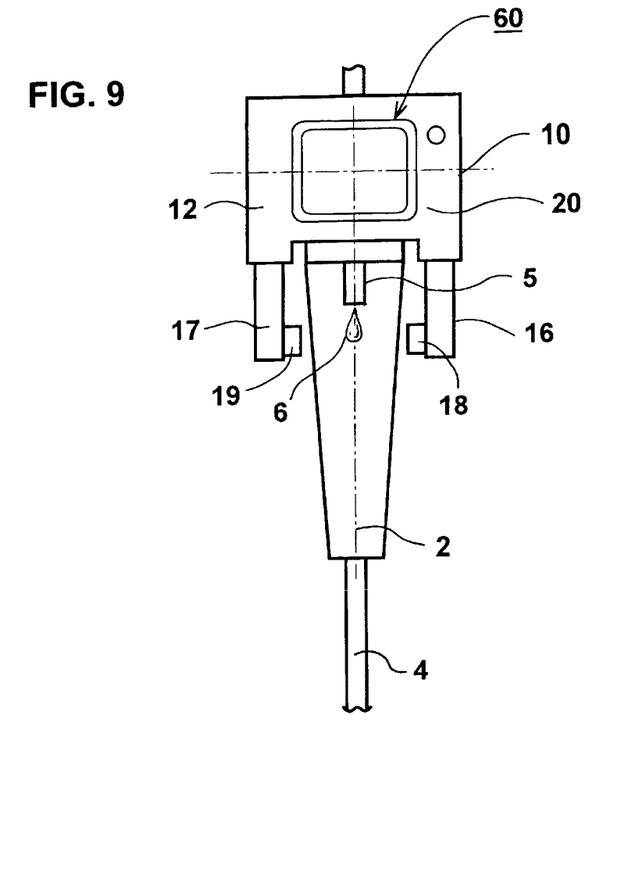
FIG. 9 is a front elevational view illustrating another form of drop monitoring unit constructed in accordance with the present invention to include a display.
Figure 10:
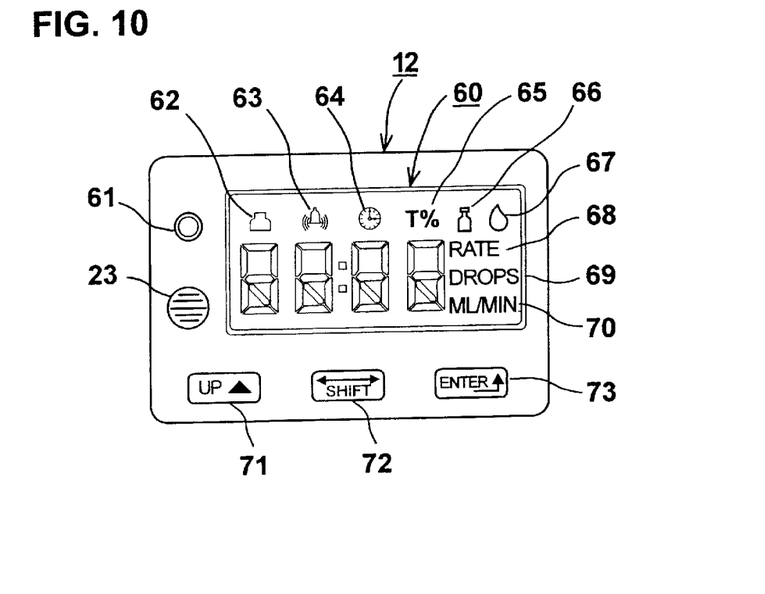
FIG. 10 illustrates the display and control panel of the drop monitoring unit of FIG. 9.
Figure 11:
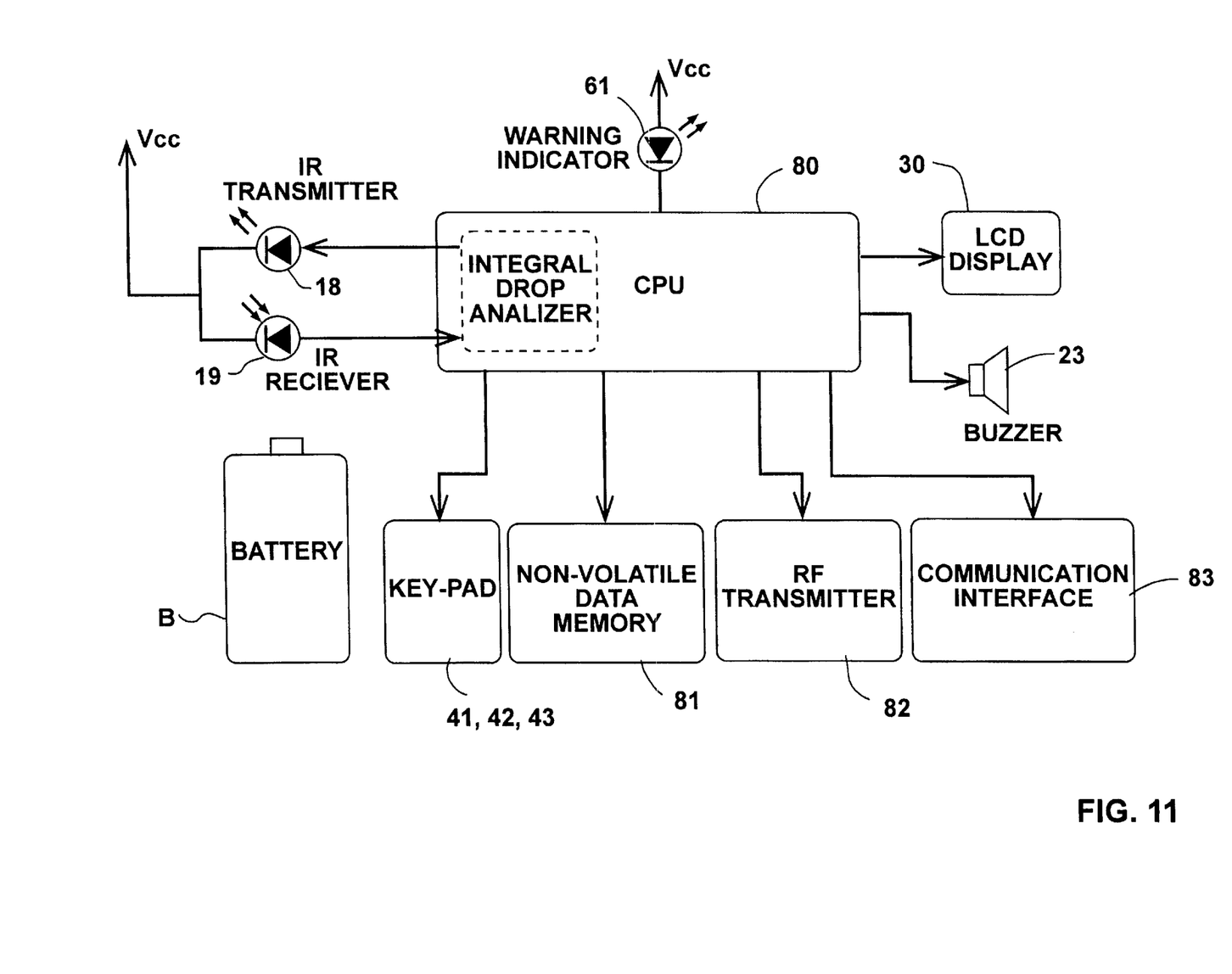
FIG. 11 is a system block diagram of the drop monitoring unit of FIGS. 9 and 10.

FIGS. 9–11 illustrate a drop monitoring unit similar to that of FIGS. 1–8, except that it is equipped to provide a number of additional functions, including an LCD display function. FIG. 10 more particularly illustrates the LCD display included in the drop monitoring unit of FIG. 9 and the control panel for that unit; whereas FIG. 11 more particularly illustrates the main electrical components included in this unit. For the sake of simplifying the description, those elements in the unit of FIGS. 9–11 which are common with those in the unit of FIGS. 1–8 are identified by the same reference numerals.

As shown particularly in FIG. 10, the front housing 12 in the unit of FIGS. 9–11 includes a four-digit alphanumeric LC display 60 for numerical data and word messages. It also includes the following indicators: alarm indicator 61, low battery indicator 62, alarm-on indicator 63, time indicator 64, tolerance (percentage) indicator 65, volume (milliliters) indicator 66, drop indicator 67, rate display (milliliters/minute) 68, drops display (accumlative) 69, and milliliter or milliliter/minute indicator 70.

The panel illustrated in FIG. 10 further includes an Up key 71, a Shift key 72, and an Enter key 73. FIG. 10 further illustrates the alarm buzzer 23, which was also included in the drop monitoring unit of FIGS. 1–8.

The main electrical components included in the drop monitoring unit are illustrated in FIG. 11. They include a processor 80 having the various inputs and outputs described above, outputs to a non-volatile memory ($E^2$) 81 for record purpose, an RF transmitter 82 for the wireless transmission of data to a central post, and a communication interface 83 for up/down loading purposes.

Processor 80 is programmed to detect drop formation as described above with respect to FIGS. 1–8, and to produce the following modes of operation:

The Up key 71 is pressed to produce a scrolling of the Menu, and the Shift key 72 is pressed to select an item in the Menu which is entered by pressing the Enter key 73.

The Menu may thus be used for selecting one of the following display STATES:

TOTAL, i.e., the total number of drops detected;
RATE, i.e., the number of drops per unit time;
VOLUME, i.e., the total number of milliliters detected;
DROPS, i.e., the total number of drops.
TIME, i.e., the elapsed time (HH:MM) from infusing starting, the system automatically returning after two seconds.

The Menu may also be used for selecting one of the following modes:

LEARN mode, as described above with respect to FIGS. 1–8, with an automatic return after one minute;
PROGRAM mode, to enable selection of the following programs:
   (a) set RATE
   (b) set ALARM RATE ON/OFF; or
   (c) set TOLERANCE RESET.

After any mode selection, the system automatically returns after ten seconds to the Display state, corresponding to the last key operation.

FIGS. 12 and 13 pictorially illustrate another drop monitor unit which also includes: a front housing 12 for the electrical circuitry, the LCD display, and the control panel; and a rear housing 13 for the electrical batteries. The monitoring unit may be mounted to the inlet tube 3 in the same manner as described above with respect to FIGS. 1–8, by means of spring element 14 mounted on the rear face of the front housing 12, and spring element 15 mounted on the front face of the rear housing 13. The rear housing 13, containing the batteries, is slidably received on guides 71, 72 integrally formed with the front housing 12, and is further formed with a central recess 83 for accommodating the inlet tube 3 to which the monitoring unit is attached.

The control panel in the monitoring unit illustrated in FIGS. 12 and 13 is somewhat different from those described above. It includes, besides the LCD display 60, an indicator 84, e.g., corresponding to indictor 61 in FIG. 10, a function key 85, an Up key 86, and a Down key 87 for presetting reference values.

In all other respects, the drop monitoring unit illustrated in FIGS. 12 and 13 may be constructed and operated as described above.

While the invention has been described with respect to several preferred embodiments, it will be appreciated that these are set forth merely for purposes of example, and that many other variations, modifications and applications of the invention may be made.

What is claimed is:

1. A self-contained drop monitoring unit attachable to, for monitoring an infusion set drop formation in an infusion set including a drip chamber to be supported in a vertical position, an inlet tube at the upper end of the drip chamber connectible to a supply of infusion liquid, and an outlet tube at the lower end of the drip chamber connectible to a patient to receive the infusion liquid; said drop monitoring unit including:

an attaching section at its upper end for attaching the drop monitoring unit to the inlet tube of the infusion set;

a pair of spaced arms depending below said attaching section to straddle the opposite sides of the drip chamber, one of said arms including a light transmitter, and the other of said arms including a light receiver for optically sensing, and for producing an electrical output corresponding to, the interruptions in the light from said light transmitter caused by the drops formed in and dropping through the drip chamber;

an electrical circuit for energizing said light transmitter and for processing the electrical output of said light receiver to produce an output related to the sensed drop formation in the drip chamber;

and a battery housing for an electrical battery for powering said electrical circuit, light transmitter and light receiver.

2. The drop monitoring unit according to claim 1, wherein said unit further includes an electrical circuit housing on the front side of said unit for housing said electrical circuit, said battery housing being on the rear side of said unit.

3. The drop monitoring unit according to claim 2, wherein said pair of spaced arms depend from one of said housings and are oriented with respect to the longitudinal axis of the drip chamber such that the light transmitter and light receiver at the lower ends of the two arms are aligned with each other and with the vertical axis of the drip chamber.

4. The drop monitoring unit according to claim 2, wherein said attaching section includes a pair of spring elements engageable with the opposite sides of the inlet tube for releasably attaching the drop monitoring unit thereto.

5. The drop monitoring unit according to claim 4, wherein said spring elements are provided with shaped recesses at their centers for receiving and gripping the inlet tube.

6. The drop monitoring unit according to claim 5, wherein one of said spring elements is carried at the rear side of said electrical circuit housing, and the other of said spring elements is carried at the front side of said battery housing.

7. The drop monitoring unit according to claim 6, wherein said battery housing with its spring element is slidably attachable to said electrical circuit housing.

8. The drop monitoring unit according to claim 1, wherein said unit further includes a display controlled by said electrical circuit for displaying the output thereof.

9. The drop monitoring unit according to claim 1, wherein said unit further includes an indicator actuatable to indicate variations in the sensed rate of drop formation with respect to a reference rate.

10. The drop monitoring unit according to claim 9, wherein said unit further includes a user input device for presetting said reference rate.

11. The drop monitoring unit according to claim 9, wherein said electrical circuit includes a processor enabling said reference rate to be preset by a "Learning" mode of operation of the processor.

12. The drop monitoring unit according to claim 9, wherein said unit further includes an audible alarm actuated when said sensed rate exceeds said reference rate.

13. The drop monitoring unit according to claim 1, wherein said electrical circuit includes:

a light modulator which controls said light transmitter to transmit light pulses;

a charging circuit enabled by said light modulator to receive the electrical output from said light receiver during the transmission of said transmitted light pulses, and to output short-width pulses in the absence of a drop and longer-width pulses in the presence of a drop;

a drop detector circuit for storing a reference time Ta corresponding to that of a reference pulse indicating the absence of a drop, for measuring the sensed time T of the pulses outputted by said charging circuit, and for determining a drop to be present when the sensed time T is greater than the reference time Ta by a predetermined amount;

and a drop rate calculator for calculating the drop rate from the output of said drop detector circuit.

14. The drop monitoring unit according to claim 13, wherein said drop detector circuit increases said reference time Ta by an amount less than said predetermined amount when the sensed time T is greater than Ta, and decreases said reference time Ta by an amount less than said predetermined amount when the sensed time T is less than Ta.

15. A drop monitoring unit for monitoring the rate of drop formation in an infusion set including a drip chamber to be supported in a vertical position, an inlet tube at the upper end of the drip chamber connectible to a supply of infusion liquid, and an outlet tube at the lower end of the drip chamber connectible to a patient to receive the infusion liquid; said drop monitoring unit including:

a light transmitter for transmitting pulses of light through said drip chamber, and a light receiver for optically sensing, and for producing an electrical output corresponding to, the interruptions in the light from said light transmitter caused by the drops formed in and dropping through the drip chamber;

and an electrical circuit for energizing said light transmitter and for processing the electrical output of said light receiver to produce an output related to the sensed rate of drop formation in the drip chamber;

said electrical circuit comprising:

a light modulator which controls said light transmitter to transmit light pulses;

a charging circuit enabled by said light modulator to receive the electrical output from said light receiver during the transmission of said transmitted light pulses, and to output short-duration pulses in the absence of a drop and longer-duration pulses in the presence of a drop;

a drop detector circuit for storing a reference time Ta corresponding to that of a reference pulse indicating the absence of a drop, for measuring the sensed time T of the pulses outputted by said charging circuit, and for determining a drop to be present when the sensed time T is greater than the reference time Ta by a predetermined amount;

and a drop rate calculator for calculating the drop rate from the output of said drop detector circuit.

16. The drop monitoring unit according to claim 15, wherein said drop detector circuit increases said reference time Ta by an amount less than said predetermined amount when the sensed time T is greater than Ta, and decreases said reference time Ta by an amount less than said predetermined amount when the sensed time T is less than Ta.

17. The drop monitoring unit according to claim 15, wherein said unit further includes an indicator actuatable to indicate variations in the monitored rate of drop formation with respect to a reference rate.

18. The drop monitoring unit according to claim 17, wherein said electrical circuit includes a processor which enables said reference rate to be preset by a "Learning" mode of operation.

19. The drop monitoring unit according to claim 15, wherein said unit further includes an attaching section at its upper end for releasably attaching the unit to the inlet tube of the infusion set, and a pair of spaced arms depending below said attaching section to straddle the opposite sides of the drip chamber, one of said arms including said light transmitter, and the other of said arms including said light receiver.

20. The drop monitoring unit according to claim 19, wherein said unit further includes a front housing on the front side of said unit for housing said electrical circuit, and a battery housing on the rear side of said unit; and wherein said pair of spaced parallel arms depend from said front housing and are oblique to the longitudinal axis of the drip chamber such that the light transmitter and light receiver at the lower ends of the two arms are aligned with each other and with the vertical axis of the drip chamber.

* * * * *